(12) United States Patent
Goswami et al.

(10) Patent No.: US 11,638,773 B2
(45) Date of Patent: May 2, 2023

(54) FLUID DISINFECTION DEVICE AND METHOD

(71) Applicant: Molekule, Inc., San Francisco, CA (US)

(72) Inventors: Dilip Goswami, San Francisco, CA (US); Jaya Rao, San Francisco, CA (US)

(73) Assignee: Molekule, Inc., San Francisco, CA (US)

( * ) Notice: Subject to any disclaimer, the term of this patent is extended or adjusted under 35 U.S.C. 154(b) by 451 days.

(21) Appl. No.: 17/074,368

(22) Filed: Oct. 19, 2020

(65) Prior Publication Data

US 2021/0030916 A1 Feb. 4, 2021

Related U.S. Application Data

(63) Continuation of application No. 16/165,975, filed on Oct. 19, 2018, now Pat. No. 10,842,907, which is a continuation of application No. 14/801,026, filed on Jul. 16, 2015, now Pat. No. 10,137,216, which is a continuation of application No. 13/403,260, filed on
(Continued)

(51) Int. Cl.
*A61L 9/20* (2006.01)
*B01D 53/86* (2006.01)
*F24F 8/22* (2021.01)
*F24F 8/167* (2021.01)

(52) U.S. Cl.
CPC .......... *A61L 9/205* (2013.01); *B01D 53/8668* (2013.01); *F24F 8/167* (2021.01); *F24F 8/22* (2021.01); *B01D 2255/20707* (2013.01); *B01D 2255/802* (2013.01); *B01D 2257/708* (2013.01); *B01D 2257/91* (2013.01); *B01D 2259/4508* (2013.01); *B01D 2259/804* (2013.01); *Y02A 50/20* (2018.01)

(58) Field of Classification Search
CPC ...................................................... A61L 9/205
See application file for complete search history.

(56) References Cited

U.S. PATENT DOCUMENTS

| 4,211,661 A | 7/1980 | Perry |
| 6,328,937 B1 | 12/2001 | Glazman |
(Continued)

FOREIGN PATENT DOCUMENTS

JP    2004-290724 A    10/2004

OTHER PUBLICATIONS

"Mechanical Resonance", Wikipedia. Screen capture from Dec. 8, 2009., Dec. 8, 2009, 1-6.

*Primary Examiner* — Donald R Spamer
(74) *Attorney, Agent, or Firm* — Jeffrey Schox; Diana Lin (57) ABSTRACT

A system for disinfecting a fluid containing contaminants (chemical and biological) includes a plurality of photocatalytic particles secured to a substrate which contacts the fluid to be disinfected. An agitator for imparting translation and/or vibrational movement is in operational communication with the substrate to increase the contact of photocatalytic particles with contaminants in the fluid. The system can include a source of photons having a wavelength corresponding to band gap energy of the photocatalytic particles to illuminate the substrate. Although the invention can be used to disinfect air in air supply registers of a heating, ventilating and air conditioning system, or in air ducts, the disinfection of any fluid (including water) is contemplated.

20 Claims, 9 Drawing Sheets

Related U.S. Application Data

Feb. 23, 2012, now abandoned, which is a continuation of application No. PCT/US2011/063637, filed on Dec. 7, 2011.

(60) Provisional application No. 61/423,931, filed on Dec. 16, 2010.

(56) References Cited

U.S. PATENT DOCUMENTS

| | | |
|---|---|---|
| 6,423,638 B1 | 7/2002 | Vanell |
| 6,675,425 B1 | 1/2004 | Iimura |
| 10,137,216 B2 | 11/2018 | Goswami et al. |
| 10,183,187 B2 | 1/2019 | Li |
| 2003/0026585 A1 | 2/2003 | Iimura |
| 2005/0061656 A1 | 3/2005 | Benoit et al. |
| 2005/0126428 A1 | 6/2005 | Lee et al. |
| 2006/0138037 A1 | 6/2006 | Yang et al. |
| 2008/0031783 A1 | 2/2008 | Briggs et al. |
| 2008/0112845 A1 | 5/2008 | Dunn et al. |
| 2008/0286163 A1 | 11/2008 | Garfield et al. |

FLUID DISINFECTION DEVICE AND METHOD

CROSS REFERENCE TO RELATED APPLICATIONS

This application is a continuation of U.S. patent application Ser. No. 16/165,975 filed 19 Oct. 2018, which is a continuation of U.S. patent application Ser. No. 14/801,026, filed 16 Jul. 2015, which is a continuation of U.S. application Ser. No. 13/403,260, filed 23 Feb. 2012, which application is a continuation of PCT International Application serial number PCT/US2011/063637, filed 7 Dec. 2011, which claims the benefit of U.S. Provisional Application Ser. No. 61/423,931, filed 16 Dec. 2010, each of which is incorporated in its entirety by this reference.

BACKGROUND OF THE INVENTION

There are several conventional methods for the cleanup and mitigation of fluid contaminants and more specifically indoor air contaminants, including, HEPA filters, electrostatic filters, biochemical filters, UV light, and ozonation. Photocatalytic oxidation (PCO) is a relatively new method that has been shown to be effective for disinfection of microorganisms and detoxification of volatile organic compounds (VOCs). The process involves the use of a photocatalyst in the presence of light of appropriate wavelength to oxidize organic compounds and microorganisms in fluids.

PCO involves the use of a photocatalyst such as Titanium Oxide (TiO2) for the destruction of hydrocarbons and microorganisms in fluids. TiO2 is a semiconductor photocatalyst with room-temperature band gap energy of about 3.2 eV. When this material is irradiated with photons having wavelengths less than about 385 nm (UV), the band gap energy is exceeded and electrons are generated through promotion from the valence band to the conduction band which results in the generation of electron holes (h+). The resulting highly-reactive electron-hole pairs have lifetimes in the space-charge region of the photocatalyst that enables participation m chemical reactions. The most widely postulated chemical reactions are:

$$OH^- + h^+ \rightarrow OH \text{(hydroxyl radical)} \quad (1)$$

$$O_2 + e^- \rightarrow O_2^- \quad (2)$$

Hydroxyl radicals and super-oxides ions are highly reactive species that can readily oxidize volatile organic compounds (VOCs) adsorbed on catalyst surfaces. They can also kill and oxidize adsorbed bioaerosols. The process is a form of heterogeneous photocatalysts, or more specifically PCO.

Several attributes of PCO make it a strong candidate for indoor air quality systems. Pollutants, particularly VOCs, are preferentially adsorbed on photocatalytic surfaces and oxidized primarily to carbon dioxide (CO2). Thus, rather than simply changing the phase and concentrating the contaminant, the absolute toxicity of the treated air stream is reduced, allowing the photocatalytic reactor to operate as a self-cleaning filter.

Photocatalytic reactors may be integrated into new and existing heating, ventilation, and air conditioning (HVAC) systems due to their modular design, room temperature operation, and generally negligible pressure drop. PCO reactors also feature low power consumption, potentially long service life, and low maintenance requirements. These attributes contribute to the potential of PCO technology to be an effective process for removing and destroying low level pollutants in indoor air, including bacteria, viruses and fungi.

However, pollutant molecules or microbes need to come in contact with the catalytic surface as these electron-hole pairs are generated for any oxidation to occur. The probability of that happening in the fluid flow stream is very low. Current designs have a low efficiency in contaminant elimination since many contaminants in the fluid bypass or occur outside the reaction sites and survive on in the fluid. The source of the problem, as discovered by the inventor, is lack of contaminant contact with the catalyst reaction sites. This invention provides such an improved and useful method to bring these contaminants in contact with the catalyst reaction sites.

SUMMARY OF INVENTION

In a first illustrative embodiment the invention includes a device and system for decontaminating a fluid. The invention of this embodiment has a predetermined path of fluid travel with at least one substrate, such as a woven or non-woven fibrous media formed in a porous lattice, positioned therein. The substrate further comprises at least one photocatalytic particle disposed on the surface thereof for generating electron-hole pairs. At least one of the photocatalytic particle is selected from the group consisting of metal oxides (doped and/or intrinsic) including Tio2, Bho3, WQ3, ZnO, FeO, SnO and Sio2 and metal oxide alloys. A photon source is positioned to contact the substrate with photons having a wavelength corresponding to at least a band gap energy of the at least one photocatalytic particle. Preferably, the substrate has at least one fixed loci relative to the path of fluid travel. At least one portion of the substrate is movable between a first position and at least a second position within the conduit.

The device also includes an agitator adapted to cause movement of the substrate between the first position and at least second position by imparting internal translation or vibration of the substrate. Translation is achieved in one embodiment by imparting a varying electric and/or magnetic field around metallic particles on the substrate (other than the fixed loci).

Alternatively, the agitator imparts external translation or vibration of the substrate. External movement can be caused by creating or agitating (increasing turbulence of) the movement of the fluid contacting the substrate. The agitator can also be an ultrasonic wave generation device, capable of creating an ultrasonic wave which approximates the natural frequency of the substrate, in communication with substrate.

In yet another embodiment the system and device for decontaminating a fluid includes a predetermined path of fluid travel with at least one substrate, movable between a first position and at least a second position within the conduit, positioned therein. At least one photocatalytic particle is disposed on the substrate for generating electron-hole pairs in the presence of light and an agitator is adapted to cause movement of the substrate between a first position and at least a second position. Here, the substrate is preferably of a solid construction selected from the group consisting of woven fibrous media, non-woven fibrous media, corrugated structures, a planar structure have a plurality of channels with a predefined cross-section and a substantially tubular container.

As with previous embodiments, the agitator imparts internal translation or vibration of the substrate. For example; where the substrate further comprises a metallic particle on a portion thereof, the agitator imparts a varying electrical field around the substrate. The agitator can also impart external translation or vibration of the substrate. For example, the agitator can be a fan or blower which creates movement of the fluid into contact with the substrate. A device can be placed between the fan and substrate to increase turbulence. The agitator can also be an ultrasonic wave generation device, capable of creating an ultrasonic wave which approximates the natural frequency of the substrate, in communication with the substrate.

In still another embodiment, the device for decontaminating a fluid includes a frame having a plurality of substrates coated with a plurality of photocatalytic particles for generating electron-hole pairs. At least one of the substrates coated with a plurality of photocatalytic particles has at least one fixed loci relative to the frame. Moreover, the at least one of the substrates coated with a plurality of photocatalytic particles has at least one fixed loci relative to the frame is movable between a first position and at least a second position. The plurality of substrates coated with a plurality of photocatalytic particles is comprised of a fibrous media arranged in a porous lattice and can be of woven fibrous media and non-woven fibrous media.

At least one of the substrates coated with a plurality of photocatalytic particles has at least one unconstrained end. In one embodiment, the at least one unconstrained end of the substrate coated with a plurality of photocatalytic particles is movable between a first position and at least a second position within the frame. Alternatively, the at least one unconstrained end of the substrate coated with a plurality of photocatalytic particles is movable between a first position and at least a second position and extends outwardly from the frame. Preferably, the at least one of the plurality of substrates coated with a plurality of photocatalytic particles is in operational communication with a means for imparting translational or vibrational motion to the at least one substrate.

BRIEF DESCRIPTION OF THE DRAWINGS

For a fuller understanding of the invention, reference should be made to the following detailed description, taken in connection with the accompanying drawings, in which:

FIG. 3C is a diagrammatic view showing the movement of the photocatalytic particle bearing fibers of an alternate embodiment of the invention, which are constrained at both ends and free there between;

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
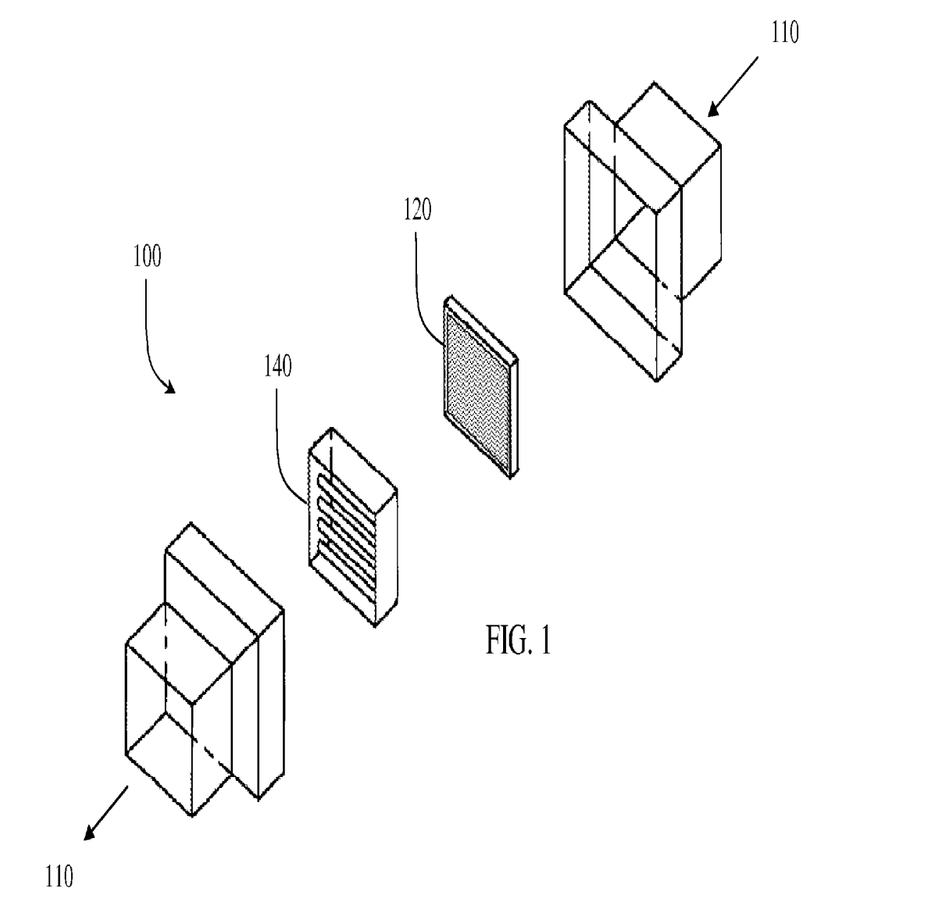
FIG. 1 is a schematic representation of an illustrative embodiment of the invention.

An illustrative embodiment of the invention is shown in FIG. 1 and includes a system for the disinfection of a fluid, generally denoted with numeral 100. FIG. 1 represents a typical HVAC system for a building incorporating the photocatalytic disinfection system of the present invention. In most systems, a fan (or blower), not shown, causes air within the building to be drawn into a duct system and passed over heating or cooling coils before being returned to the building. Here, system 100 includes substrate 120 in optical communication with photon source 140 placed in the path of travel (110) of the fluid to be disinfected. Path of travel 110 is preferably defined by a conduit such as the ductwork of air handling system Substrate 120 further includes a plurality of photocatalytic particles (not shown) on its surface. The photocatalytic particles are comprised of metal oxides and/or metal oxide alloys. Although any photocatalytic particle capable of generating electron-hole pairs in the presence of light can be used, the photocatalytic particles are generally selected from the group consisting of $TiO_2$, $BhO_3$, $WQ_3$, $ZnO$, $FeO$, $SnO$ and $SiO_2$. In a preferred embodiment, the photocatalytic particles are doped or intrinsic $TiO_2$.

The photocatalytic particles generate electron-hole pairs when contacted with photons from photon source 140. At least a portion of the photons emitted by photon source 140 have an energy at least equal to the band gap energy of the photocatalyst. In a preferred embodiment, photon source 140 delivers low energy photons of the UV-A and lower energy portion of the UV-B spectrum. A UV wavelength between about 300 and 400 nm is preferred. Photon sources of 14 W can be used, emitting approximately 1.5 W of UV-radiation, at about 350 nm.

In another variation, photon source 140 may be either emitted or transmitted by one or more fiber optic elements within a network of fibers. These fibers may be electrically excited in order to provide the photons or the photons can be reflected by means of a fiber optics extended light source. The fiber optics arrangement can bring photons of light by way reflecting and refracting photons through a guided path.

These photons are then directed at the photocatalytic particles. The light source may be naturally occurring or an artificial form of light.

Figure 2:
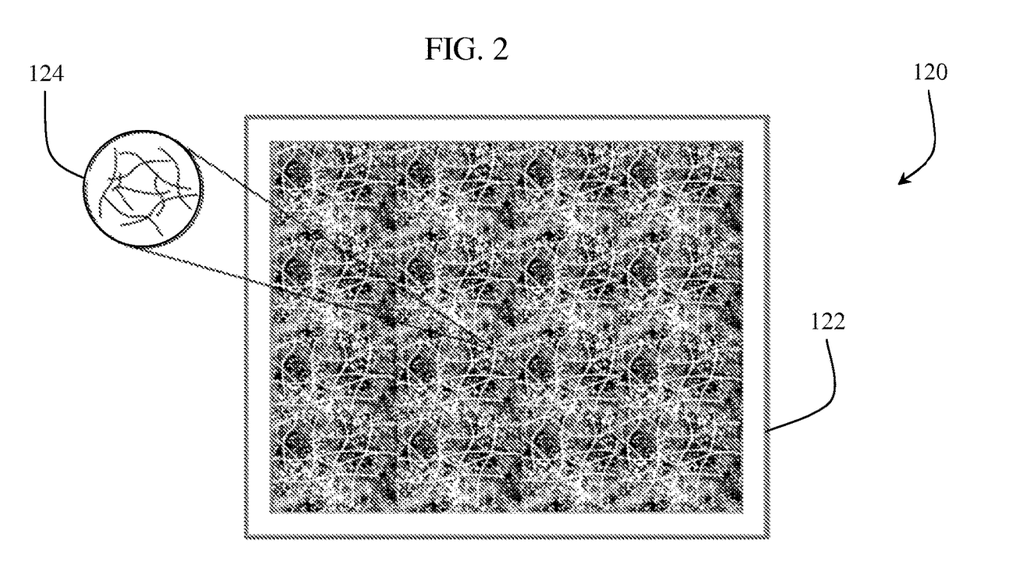
FIG. 2 is a perspective view of the first variation of the fibers of the first embodiment, which form a filter.
Figure 4:
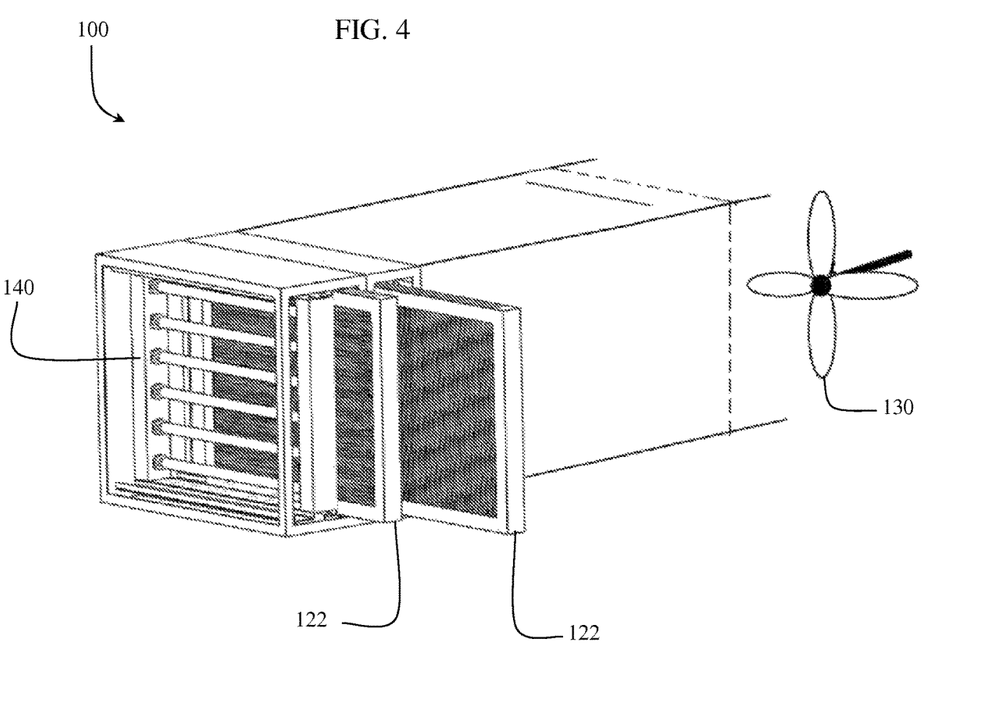
FIG. 4 is a diagrammatic view illustrating the photon source, the filter containing the photocatalytic bearing fibers, and the agitator, in the form of a fan, in series within an air conditioning unit.

In one embodiment, as shown in FIG. 2, substrate 120 is a filter 122 comprising fibers 124 such as commonly found in air conditioning filters. Preferably the fibers are composed of cotton, wool, polymers, metals, metal oxides, or carbon fibers and may be woven or non-woven to form a porous lattice. In this embodiment, the fibers function as the surface upon which the photocatalytic particles are attached. Filter 122 comprising fibers 124 is positioned within the fluid path of travel allowing the fluid to move over fibers 124 as it passes through filter 122. This allows contaminants in the fluid to contact the photocatalytic particles. A single filter 122 can be used or a series of filters can be stacked in series (as shown in FIGS. 4-6 below).

Figure 3A:
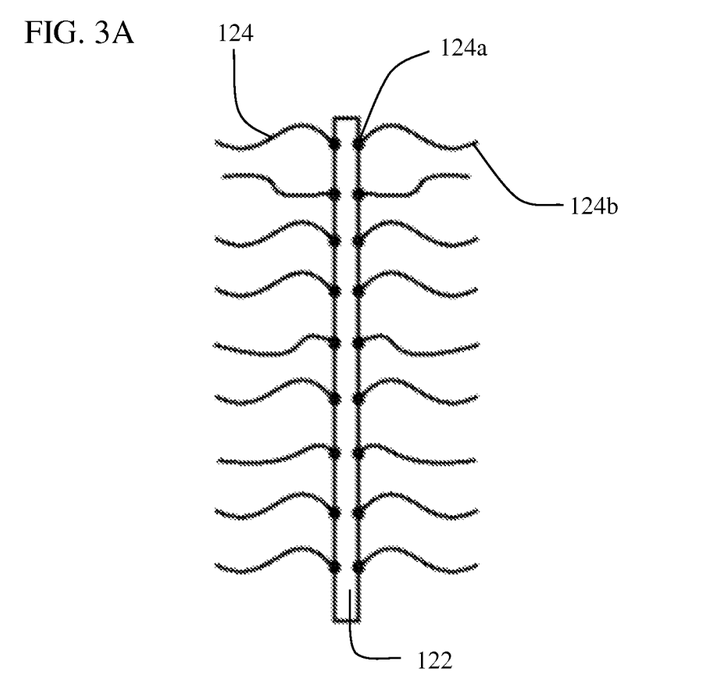
FIG. 3A is a detailed view of the photocatalytic particle bearing fibers of one embodiment of the invention, which are constrained at one end and free at an opposing end.
Figure 3B:
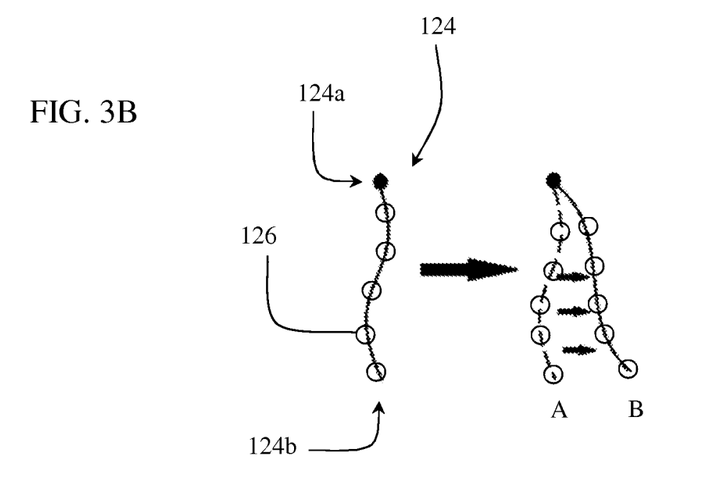
FIG. 3B is a diagrammatic view showing the movement of the photocatalytic particle bearing fibers of FIG. 3A, which are constrained at one end and free at an opposing end.
Figure 3C:
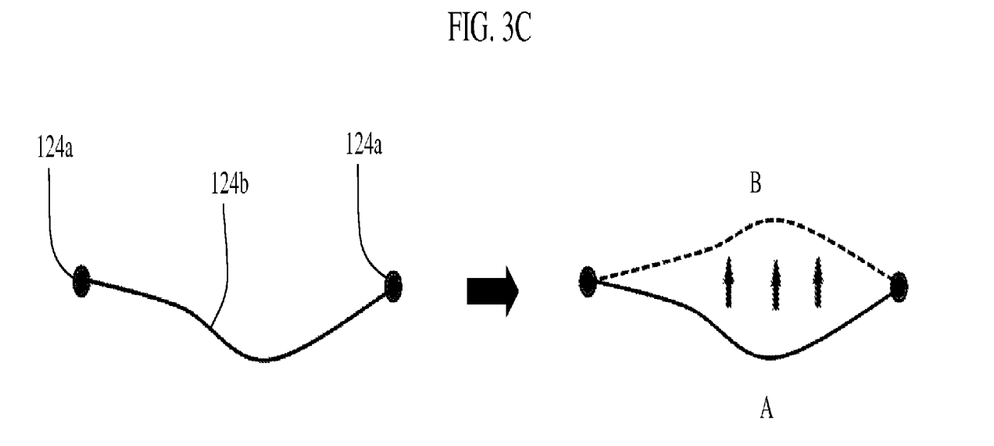

It is also possible to arrange fibers 124 to allow the movement thereof with respect to filter 122. As shown in FIGS. 3A and 3B, fiber 124 of one embodiment is constrained by filter 122 at fixed loci 124a whereas free end 124b remains unconstrained. When agitated, either externally or internally, fiber 124 moves from first position (A) to second position (B). Furthermore, as shown in FIG. 3C, fiber 124 can have more than one fixed loci 124a with unconstrained portion 124b there between. So long as fiber 124 is made of a sufficiently pliable material, agitation will cause unconstrained portion 124b to move between first position A and second position B. This "waving" motion increases the amount of contaminants within the passing fluid which come in contact with photocatalytic particles 126. Fibers 124 can be arranged in a woven/non-woven porous lattice within filter 122 or can extend outward from filter 122 into the fluid path of travel.

Motion, e.g. translation or vibration, can be imparted on the fibers by an agitation device through external or internal means. Although specific examples are provided below and FIGS. 4 through 5, agitator 130 can be any device which imparts translational or vibrational movement of the fiber(s) from a first position to a second position. In the illustrative embodiment of FIG. 4, agitator 130 is the fan or blower which moves air through an air conditioning system. Sufficiently pliable fibers will "blow in the breeze" as the fluid to be disinfected passes over and through filter 122. Additionally, a mechanical means such as a substantially rigid grid or frame (not shown) can be placed between the fan (agitator 130) and filter 122 to increase the turbulence of the fluid as it passes through filter 122. This increased turbulence will produce an increased waving motion of the fibers Filter 122 can also be adapted to rotate within path of travel 110. Rotational movement can be imparted upon filter 122 either through external mechanical means, such as by a dedicated motor. Rotational movement can also be imparted by the resistance of the fluid passing through filter 122.

Figure 5:
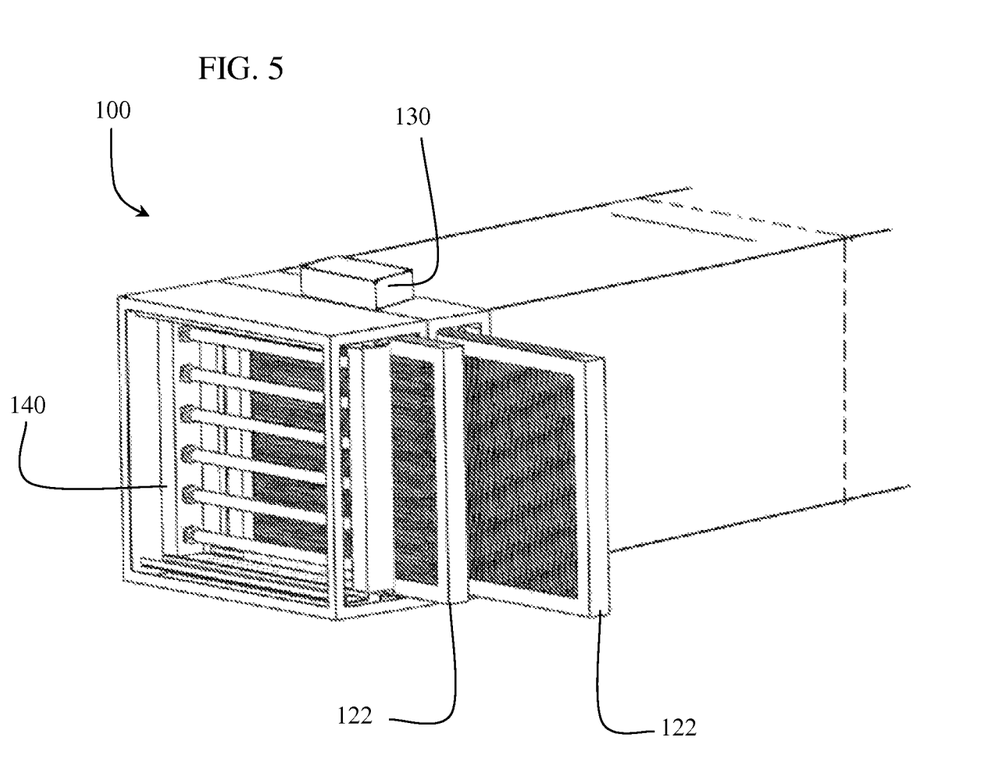
FIG. 5 is a diagrammatic view illustrating the photon source, the filter containing the photocatalytic bearing fibers, and the agitator, in the form of an ultrasonic wave generator, in series within an air conditioning unit.
Figure 6:
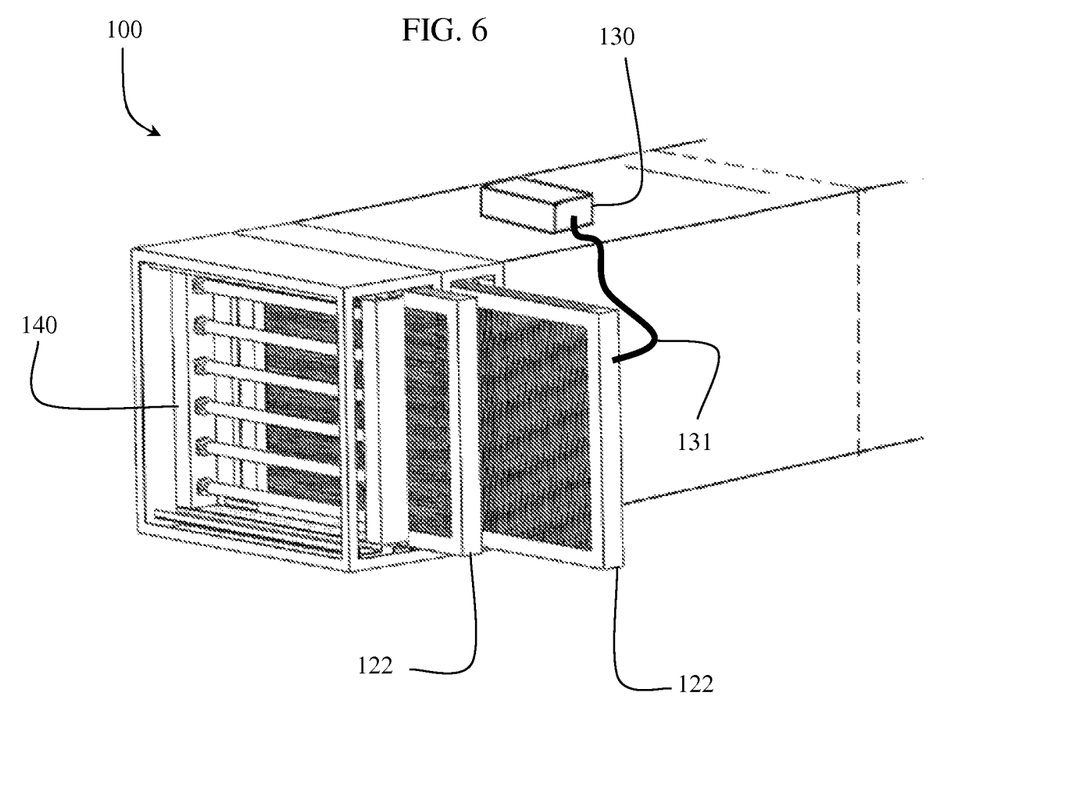
FIG. 6 is a diagrammatic view illustrating the photon source, the filter containing the photocatalytic bearing fibers, and the agitator, in the form of an electric current controller in communication with the filter, in series within an air conditioning unit.

Alternatively, as shown in FIG. 5, agitator 130 can be an ultrasonic wave generator disposed in communication with the fibers of the filter. The ultrasonic waves resonate with the natural frequency of the fibers causing translation or vibration thereof.

Motion can also be imparted on fibers 124 through electrical means. In the embodiment shown in FIG. 6, at least some of the fibers are electrically conductive, such as metal fibers, electrically conducting polymer fibers, electrically conducting carbon fibers or carbon nanotubes. If non-conductive fibers are used, a portion thereof can be coated with a conductive material such as aluminum. In use, agitator 130 includes a controller which applies a varying electrical pulse to fibers through wire 131 connected to filter 122 to cause vibrational movement therein.

In still another alternative embodiment, motion is imparted on fibers 124 through magnetic forces. In this embodiment, at least some of the fibers, such as metal fibers, comprise a magnetic element. If non-magnetic fibers are used, a portion thereof can be coated with a magnetic material. In use, a varying electrical field is created around the fibers causing translational movement therein.

Figure 7:
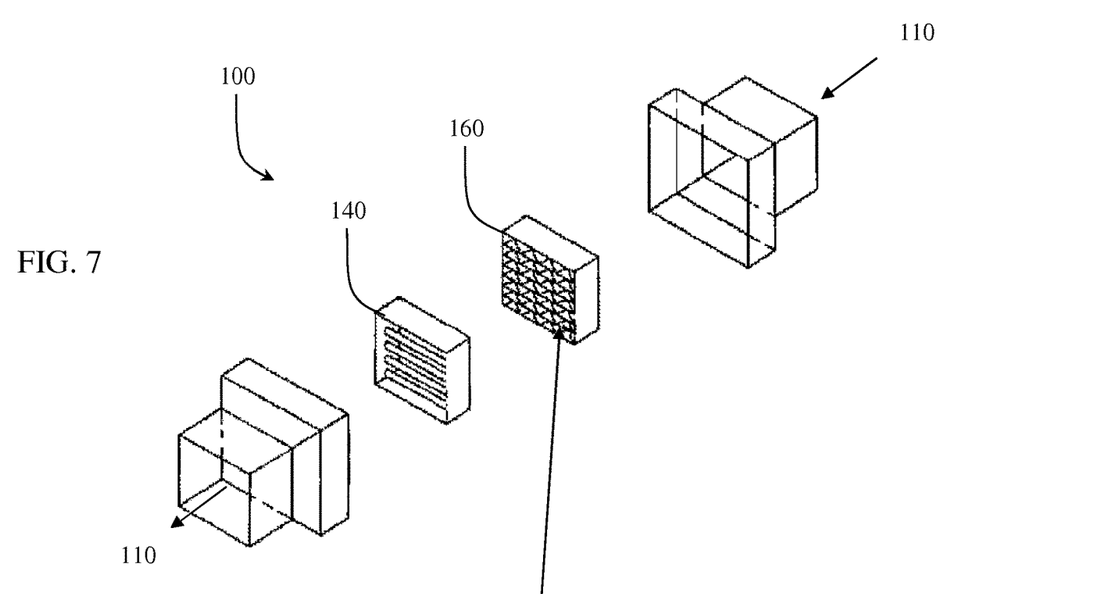
FIG. 7 is a schematic representation of an alternate embodiment of the invention wherein the substrate is a photocatalytic particle coated channeled structure.

Another embodiment of the invention includes a plurality of photocatalytic particles (not shown) disposed on the surface of substrate 160 in optical communication with photon source 140 placed in the path of travel (110) of the fluid to be disinfected. The schematic representation of this embodiment is shown in FIG. 7.

Figure 8:
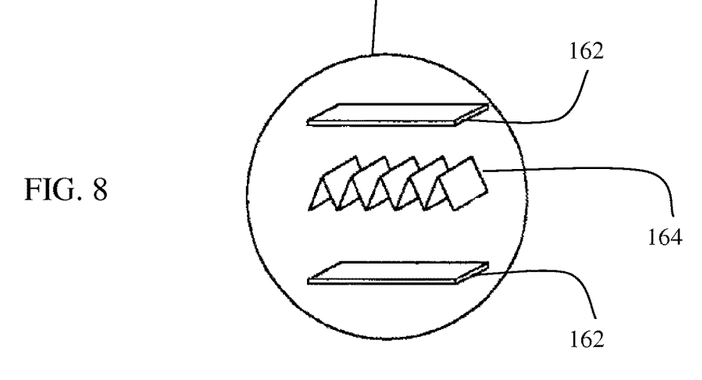
FIG. 8 is a detailed view of one embodiment of the substrate of FIG. 7.

In this illustrative embodiment, light from photon source 140 is directed toward substrate 160 which includes photocatalyst coated planar substrate elements 162 and photocatalyst covered corrugated substrate elements 164. A layer of photocatalyst particles is secured to at least one side of substrate elements 162 and 164. A photocatalyst layer can be disposed on one or both sides of substrate elements 162 and 164. The space between the substrate elements provides channels with sufficient space for the fluid to pass there through with a minimal drop in pressure.

Alternatively, substrate 160 can comprise channels of any cross-section and is not limited to corrugated embodiments. Substrate 160 can also be formed of fabric such as cotton, wool, vinyl, or silk material. Substrate 160 can also include materials that are toxic to micro-organisms such as silver.

As with the embodiments discussed above, an agitator (not shown) imparts translational or vibrational movement to substrate 160. Substrate 160 of this embodiment functions as an object upon which the photocatalyst particles can be secured. Photocatalyst particles secured onto the surfaces can then react with impinging photons to generate electron hole pairs. Motion imparted onto these surfaces helps to bring the electron hole pairs in contact with contaminants in the fluid. Examples of such agitation include, but are not limited to, displacement of substrate 160 within a predefined range of motion caused by the movement of the fluid to be disinfected, a varying magnetic field created around substrate 160 wherein at least a portion thereof comprises magnetic elements and passing an electrical current through substrate 160 wherein at least a portion thereof comprises electrically conductive elements.

Figure 9:
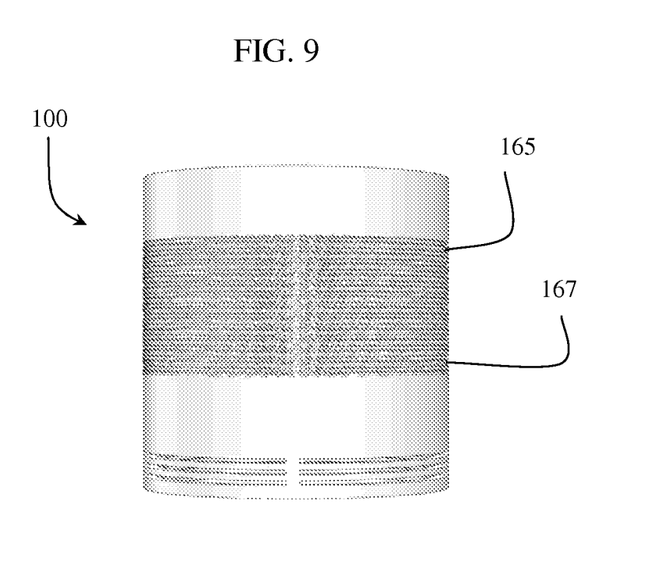
FIG. 9 is a perspective view of an embodiment of the invention wherein the photocatalytic particle coated substrate is a tubular container.
Figure 10:
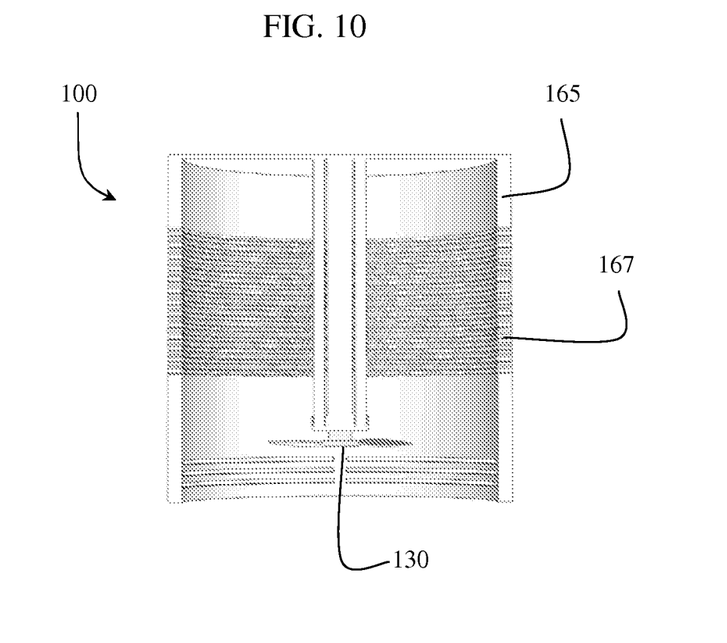
FIG. 10 is a section view of the tubular container of FIG. 9.

In another variation, substrate 160 is disposed in the form a container 165. Container 165 may be tubular as shown in FIGS. 9 and 10. Container 165 may further contain lattice of holes 167 for fluid circulation.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

For example; although the examples shown above illustrative a fluid disinfection device for use in a standard air condition system, The present invention can be applied to, but is not limited to, air filtration, detoxification and disinfection for users in a building, room or a confined space, such as an airplane or a car. The invention may also be used for disinfection of other fluids, such as water. The system may be applied to material disinfection as well, where the photocatalytic particles are coated onto the materials.

It is also to be understood that the following claims are intended to cover all of the generic and specific features of the invention herein described, and all statements of the scope of the invention which, as a matter of language, might be said to fall there between.

The invention claimed is:

1. A method for decontaminating a fluid using a filter comprising a fiber, wherein the fiber defines a cross-sectional area, the method comprising:
    agitating the fiber with an agitator between a first position and a second position to sweep an area greater than the cross-sectional area in a direction normal to a path of fluid travel proximal the filter, wherein the filter is fixed and a first end of the fiber is fixed to the filter, wherein a second end of the fiber is freely moveable within the path of fluid travel.

2. The method of claim 1, wherein the fiber further comprises a metallic particle disposed on a portion of the fiber distal the first end.

3. The method of claim 2, wherein agitating the fiber comprises applying an electrostatic force to the metallic particle by providing a varying electric field proximal the fiber.

4. The method of claim 1, wherein the fiber further comprises a photocatalytic particle disposed on the fiber between the first and second ends, wherein the method further comprises illuminating the photocatalytic particle with optical radiation having a wavelength corresponding to at least a band gap energy of the photocatalytic particle.

5. The method of claim 4, wherein the fiber further comprises silver.

6. The method of claim 4, wherein a material of the photocatalytic particle comprises at least one of metal oxides or metal oxide alloys.

7. The method of claim 6, wherein the material of the photocatalytic particle comprises at least one of doped $TiO_2$, intrinsic $TiO_2$, $Bi_2O_3$, $WO_3$, ZnO, FeO, SnO or $SiO_2$.

8. The method of claim 1, wherein the fiber further comprises a magnetic particle disposed on a portion thereof distal the first end;
    wherein agitating the fiber comprises applying an electromagnetic force to the magnetic particle by varying a magnetic field proximal the fiber.

9. The method of claim 1, wherein the fiber defines a natural frequency, wherein agitating the fiber comprises applying an ultrasonic wave to the fiber, wherein the ultrasonic wave comprises a frequency that approximates the natural frequency.

10. The method of claim 1, wherein the filter further comprises a second fiber having a corresponding first end fixed to the filter, a corresponding second end fixed to the filter, and a flexible portion between the first end and the second end, wherein the method further comprises agitating the flexible portion between a corresponding first position and a corresponding second position within the path of fluid travel.

11. A method for decontaminating a fluid-using a filter comprising a fiber, wherein the fiber defines a cross-sectional area, the method comprising:
    agitating the fiber with an agitator between a first position and a second position to sweep an area greater than the cross-sectional area in a direction normal to a path of fluid travel proximal the filter, wherein the filter is fixed and a first end and a second end of the fiber are fixed to the filter, wherein the fiber comprises a flexible portion between the first end and the second end.

12. The method of claim 11, wherein the fiber further comprises a metallic particle disposed on a portion of the fiber distal the first end.

13. The method of claim 12, wherein agitating the fiber comprises applying an electrostatic force to the metallic particle by providing a varying electric field proximal the fiber.

14. The method of claim 11, wherein the fiber further comprises a photocatalytic particle disposed on the fiber between the first and second ends, wherein the method further comprises illuminating the photocatalytic particle with optical radiation having a wavelength corresponding to at least a band gap energy of the photocatalytic particle.

15. The method of claim 14, wherein a material of the photocatalytic particle comprises at least one of metal oxides or metal oxide alloys.

16. The method of claim 15, wherein the material of the photocatalytic particle comprises at least one of $TiO_2$, $Bi_2O_3$, $WO_3$, ZnO, FeO, SnO or $SiO_2$.

17. The method of claim 16, wherein the material of the photocatalytic particle comprises at least one of doped $TiO_2$ particles or intrinsic $TiO_2$ particles.

18. The method of claim 11, wherein the fiber further comprises a magnetic particle disposed on a portion thereof distal the first end;
    wherein agitating the fiber comprises applying an electromagnetic force to the magnetic particle by varying a magnetic field proximal the fiber.

19. The method of claim 1, wherein the fiber defines a natural frequency, wherein agitating the fiber comprises applying an ultrasonic wave to the fiber, wherein the ultrasonic wave comprises a frequency that approximates the natural frequency.

20. The method of claim 11, wherein the filter further comprises a second fiber having a corresponding first end fixed to the filter and a corresponding second end freely movable within the path of fluid travel between a corresponding first position and a corresponding second position.

* * * * *